United States Patent [19]

Abatjoglou

[11] Patent Number: 5,196,596
[45] Date of Patent: Mar. 23, 1993

[54] HIGHER ALDEHYDE SEPARATION PROCESS

[75] Inventor: Anthony G. Abatjoglou, Charleston, W. Va.

[73] Assignee: Union Carbide Chemicals & Plastics Technology Corporation, Danbury, Conn.

[21] Appl. No.: 813,528

[22] Filed: Dec. 26, 1991

[51] Int. Cl.$^5$ .................... C07C 45/78; C07C 45/81
[52] U.S. Cl. ................................. 568/492; 568/491
[58] Field of Search .............. 568/467, 491, 492, 875

[56] References Cited

U.S. PATENT DOCUMENTS

| | | | |
|---|---|---|---|
| 3,542,879 | 11/1970 | Dinwoodie et al. | 568/492 |
| 4,041,081 | 8/1977 | Bexten et al. | 260/601 |
| 4,191,710 | 3/1980 | Leacock | 568/492 |
| 4,480,139 | 10/1984 | Scott et al. | 568/492 |
| 4,510,332 | 4/1985 | Matsumoto et al. | 568/454 |
| 4,523,038 | 6/1985 | Scott et al. | 568/492 |
| 4,633,021 | 12/1986 | Hanes | 568/454 |
| 4,670,606 | 6/1987 | Romano et al. | 568/410 |
| 4,678,857 | 7/1987 | Dureanleau | 568/492 |
| 4,731,486 | 7/1989 | Abatjoglou et al. | 568/454 |

FOREIGN PATENT DOCUMENTS

| | | |
|---|---|---|
| 1041940 | 10/1958 | Fed. Rep. of Germany . |
| 0350922 | 7/1989 | Fed. Rep. of Germany . |
| 52-053952 | 4/1977 | Japan . |

OTHER PUBLICATIONS

STN International, Registry File Search Results, for Compounds Having the Registration Numbers: RN 63947-34-2, RN 46463-53-0, RN 45877-14-3, RN 45808-34-2, RN 101791-75-7, RN 72854-41-2.

Synthesis (10), 920-1, 1987 by Badone, et al., "Use of Polyethylene Glycol in the Synthesis of Alkyl Fluorides from Alkyl Sulfonates".

Chemical Abstracts: CA 54:24405c CA 50:5019e.

A New Class of Broad Spectrum Antibacterials, Felton, Stephen M. and Kapp, Ira B; Felton Int. Inc., Brooklyn, N.Y. USA; TGA (Toilet Goods Assoc.) Cosmet J. 2(1), 16-19; 1970.

Flammability properties of some synthetic fragrant substances and intermediate products Kuravskaya, I. M.; Borovik, V. N., Vses. Nauchno-Issled, Inst. Nat. Dushistykh Veshch., Selo Vorontsovo, USSR, Maslo-Zhir. Prom-St., (2), 19-25, 1975.

Advanced Organic Chemistry Louis F. and Mary Fieser, Rienhold Publishing Company (New York) 1961 pp. 443-444.

Primary Examiner—Werren B. Lone
Attorney, Agent, or Firm—E. C. Trautlein

[57] ABSTRACT

This invention relates to a process for separating an aldehyde that contains at least seven carbon atoms and that is free of alpha substituents from a solution containing the aldehyde and a non-polar organic liquid which process comprises contacting the solution with water under conditions such that a solid hydrate of the aldehyde forms and separating the solid hydrate from the solution. This invention also relates to novel hydrates so produced.

10 Claims, No Drawings

HIGHER ALDEHYDE SEPARATION PROCESS

FIELD OF THE INVENTION

This invention relates to the separation of higher primary aldehydes from solutions, particularly from solutions containing the mixed aldehyde products of hydroformylation processes.

DESCRIPTION OF RELATED ART

Aldehydes that contain at least seven carbon atoms and that are free of alpha substituents (hereinafter referred to as "higher primary aldehydes") are useful in the production of flavors, fragrances, lubricants and pharmaceuticals. When so used, it is often desirable, or even essential, that the aldehydes be relatively free from other materials.

It is known that hydroformylation processes are useful in producing aldehydes from alpha olefins, carbon monoxide and hydrogen in the presence of a catalyst (e.g., a rhodium-ligand complex). Generally, such processes produce a mixture of normal aldehydes (normal aldehydes are linear primary aldehydes) and "iso" aldehydes (in the hydroformylation field, aldehydes having an alpha methyl substituent are called iso aldehydes). The mole ratio of the normal and iso aldehydes in such mixtures (usually called the N/I ratio) is often not the optimum ratio for the end use envisioned for the aldehydes. Accordingly, some means must be employed to separate the aldehydes.

When mixtures of lower normal and iso aldehydes are produced by hydroformylation processes, the normal aldehyde is fairly readily separated from the iso aldehyde by distillation. However, when mixtures of higher normal and iso aldehydes are produced, separation of mixtures of such aldehydes by distillation is not practicable due to the fact that the boiling points of the higher aldehydes are close to each other and are elevated. In addition, at such elevated temperatures, undesirable reactions (e.g., condensation of the aldehydes to produce "heavies") tend to occur to an increased extent. Hence a variety of other methods have been proposed to effect the separation of mixtures of higher normal and iso aldehydes produced by hydroformylation processes.

U.S. Pat. No. 4,041,081 discloses that mixtures of higher aldehydes produced by a hydroformylation process can be separated by selectively precipitating the normal aldehyde using, as a precipitating agent, an alkali metal hydrogen sulfite in aqueous solution which forms an insoluble addition product with the normal aldehyde. The addition product is separated by filtration and the higher normal aldehyde is regenerated by reacting the addition product with a carbonyl compound containing from one to four carbon atoms. The regenerated normal aldehyde contains solvent, carbonyl compounds and high boiling polymer aldehydes from which the regenerated normal aldehyde is separated by distillation. U.S. Pat. No. 4,523,038 discloses a similar separation using an alpha, omega $C_2$ to $C_{12}$ linear alkane diol as the precipitating agent which forms an adduct with the normal aldehyde. The adduct is separated by filtration and the normal aldehyde is regenerated by thermally decomposing the adduct or by reacting the adduct with water, an acid or a base.

U.S. Pat. No. 4,670,606 discloses that mixtures of higher aldehydes produced by a hydroformylation process can be separated by dissolving the mixture in a liquid hydrocarbon solvent containing from 3 to 5 carbon atoms or in tertiary-butylether and cooling the solution to $-20°$ C. to $-52°$ C. so as to selectively precipitate the higher normal aldehyde.

U.S. Pat. No. 4,510,332 discloses that mixtures of higher aldehydes (specifically nonanedials) produced by a hydroformylation process can be separated by selectively extracting the higher normal aldehyde from the mixture using, as the extractant, either a primary alcohol containing about 5 to 11 carbon atoms or a mixture of said primary alcohol and a saturated aliphatic hydrocarbon containing about 5 to 10 carbon atoms. The extract layer contains a dialkyl hemiacetal of the normal nonanedial which is precipitated by washing the extract layer with water. The normal nonanedial is regenerated by distilling the precipitate.

A common feature of the above-described separation procedures is that they involve the use of an additional material or materials (e.g., a solvent, precipitant or an extractant) that may be fairly expensive and/or that may itself not be readily separated from the higher normal aldehyde.

It is an object of the present invention to provide a process for separating higher normal aldehydes from non-polar organic liquids (e.g., iso aldehydes) using an inexpensive material that is readily separated from the aldehyde.

It is a further object of the present invention to provide novel solid hydrates of higher normal aldehydes.

SUMMARY OF THE INVENTION

This invention provides a process for separating an aldehyde that contains at least seven carbon atoms and that is free of alpha substituents from a solution containing the aldehyde and a non-polar organic liquid which process comprises contacting the solution with water under conditions such that a solid hydrate of the aldehyde forms and and separating the solid hydrate from the solution.

DESCRIPTION OF THE PREFERRED EMBODIMENTS

The higher primary aldehydes separated from solutions by the process of the present invention are aldehydes that contain at least seven carbon atoms and that are free of alpha substituents. In this context, "primary aldehyde" denotes a compound having the formula:

$$R-\underset{\underset{H}{|}}{\overset{\overset{H}{|}}{C}}-\overset{\overset{H}{|}}{C}=O \qquad \text{Formula (I)}$$

wherein R is a monovalent organic group, e.g., a substituted or unsubstituted, linear, branched or cyclic aliphatic or aromatic monovalent group containing at least five carbon atoms. When R in Formula (I) is a linear aliphatic group, the primary aldehyde is a normal aldehyde. Preferably, R in Formula (I) contains from 5 to 25 inclusive, or more preferably from 5 to 15 inclusive, carbon atoms. R is preferably a hydrocarbyl group (i.e., a monovalent hydrocarbon group) and, more preferably, an alkyl group or an aryl-substituted alkyl group.

The process of the present invention is generally applicable to separating any higher primary aldehyde from any solution containing the aldehyde and a non-polar organic liquid. Such solutions include the crude reaction products of the processes, especially hydroformylation processes, used to produce the higher primary aldehydes. In the case of the crude reaction products of hydroformylation processes, the solutions contain (as the non-polar organic liquids) unreacted olefins, higher iso aldehydes, saturated hydrocarbons produced by reduction of the olefin and heavies (aldehyde condensation products). The solutions can also contain polar materials (e.g., ligands that formed part of the hydroformylation catalyst) and catalyst metals (e.g., rhodium). The iso aldehydes in such crude hydroformylation reaction products are represented by the formula:

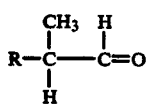

Formula (II)

wherein R has the meaning defined for Formula (I) above. The crude hydroformylation reaction products can be produced by any known process (e.g., by the processes described in U.S. Pat. Nos. 4,633,021 and 4,731,486.

In the event the crude hydroformylation reaction products contain substantial amounts of polar materials, it is preferred that the polar materials be separated from the reaction products before the reaction products are used in the process of the present invention. By way of illustration U.S. Pat. Nos. 4,633,021 and 4,731,486 disclose crude hydroformulation reaction products containing ionically charged phosphorus ligands. It is preferred that such ligands be separated from the reaction products (e. g., by the process disclosed in published European Patent Application 350,922) before the reaction products are used in the process of this invention.

The ligand separation process of the above-mentioned European Patent Application involves separating the reaction product into an aqueous phase containing the ionically charged phosphorous ligand and an organic phase containing the higher primary aldehyde, its isomer, unreacted olefin, olefin reduction products and heavies. The organic phase so obtained can be used in the process of this invention. In the ligand separation process of the European Patent Application, the crude hydroformylation reaction product is mixed with water or both water and an additional non-polar hydrocarbon compound (e.g., a $C_6$ to $C_{30}$ alkane) to effect the phase separation. The phase separation should be conducted at a temperature above the decomposition temperature of the hydrate of the higher primary aldehyde (e.g., at 40° C. or above) to prevent premature formation of the hydrate and consequent clogging of the separation apparatus.

In a preferred embodiment of the present invention, the solution is modified by incorporating therein a minor amount of a polar aprotic solvent to increase the solubility of water in the solution. Suitable polar aprotic solvents include N-methyl pyrrolidone, dimethyl sulfoxide, dimethyl formamide, dimethyl sulfone, dimethyl sulfolane, acetonitrile, propionitrile and the like.

In the process of the present invention, the higher primary aldehyde reacts with water to form a solid hydrate in accordance with the equation:

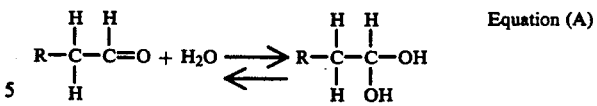

Equation (A)

wherein R has the meaning defined for Formula (I) above. Surprisingly, these hydrates are more stable than are hydrates of iso aldehydes of the same carbon content and are solids (at 25° C.). The hydrates are insoluble in non-polar organic liquids and water. By way of contrast, only a few stable hydrates have been reported in the literature and those are formed from aldehydes (e.g., trichloromethyl acetaldehyde [chloral]) which have strong electron withdrawing groups alpha to the carbonyl groups (see "Advanced Organic Chemistry" by David F. Fieser and Mary Fieser, Reinhold Publishing Corporation (1961), pages 443 and 444. Various hydrates of higher primary aldehydes are registered in Chemical Abstracts as hypothetical compounds. However, as far as is known, no higher primary aldehyde hydrates (particularly no hydrocarbyl hydrates containing from 7 to 27 carbon atoms inclusive) have actually been prepared and isolated as solids.

The process of the present invention is conducted at a temperature above the melting point of the higher primary aldehyde being separated but below the decomposition temperature of the hydrate formed by the reaction of the aldehyde with water. The preferred temperature for conducting the process is just above the melting point of the aldehyde. The amounts of water employed in the process of the present invention is from 1 to 100 or more moles per mole of the higher primary aldehyde.

Once the hydrate has been formed in the practice of the process of the present invention, it can be separated from the bulk of the non-polar organic liquid by any suitable means (e.g., by filtration at or below room temperature). Owing to the oftentimes waxy consistency of the hydrate, some of the non-polar organic liquid (e.g., iso aldehyde) may remain trapped in the hydrate after filtration. Essentially all of such residual liquid can be removed from the hydrate by washing the hydrate with a suitable solvent or solvents in one or more steps. An alcohol wash (e.g., a methanol or isopropanol wash) followed by a hydrocarbon wash (e.g., a hexane wash) has proven effective in removing such residual non-polar organic liquids from the hydrate. Thereafter, the hydrate can be dried, preferably under vacuum at room temperature, to produce an essentially pure hydrate. By this means hydrates of 99% and even 99.9% purity can be obtained.

If desired, the hydrates so isolated can be stored for prolonged periods of time, provided they are maintained at or below room temperature (e.g., at −80° C. to +25° C.). When it is desired to regenerate the higher primary aldehyde, the hydrate is simply heated to a moderate temperature (e.g., from 40° C. to 120° C.) to cause the reverse of Equation (A) to occur and to volatilize the water to produce an essentially pure higher primary aldehyde.

When the solution used in the process of this invention also contains an isomer of the higher primary aldehyde (e.g., when the solution is the crude reaction product of hydroformylation process), the isomeric aldehyde remains in the solution after the higher primary aldehyde has been separated. The isomeric aldehyde can be then separated from the other components of the solution by any suitable means (e.g., distillation).

The higher primary aldehydes produced by the process of this invention can be used in the production of flavors, fragrances, lubricants and pharmaceuticals. Owing to their purity (particularly with respect to their relative freedom from isomeric aldehydes), the primary higher aldehydes are particularly useful in such applications.

The following Examples illustrate the present invention.

In the following Examples, the following abbreviations are used:
ml milliliter
° C. degrees centigrade
N/I normal to isoaldehyde ratio (moles)
% percent by weight

EXAMPLE I

This Example illustrates the formation of solid $C_7$, $C_9$, $C_{11}$, $C_{13}$ and $C_{15}$ primary aldehyde hydrates by separating the aldehydes from crude hydroformylation reaction products after the ligands had been removed from the reaction products. The hydroformylation procedure illustrated by Example 6 of published European Patent Application 350,922 was employed to produce the crude hydroformylation reaction products and also to separate from the reaction products the ionically charged ligands that had been used in the hydroformylation reactions.

After removal of the ligands, the crude hydroformylation reaction products used in this Example (and the reaction products used in the following Examples) typically had the following approximate composition:

| | |
|---|---|
| Mixed aldehydes | 80% |
| Hydrocarbon* | 5% |
| Unreacted olefin | 15% |
| Catalyst ligand | trace |
| Catalyst metal | trace |

*Produced by reduction of the olefin reactant

The following reagents were mixed in an 8 ounce wide-mouth jar which was flushed with nitrogen and capped tightly: 100 ml of nitrogen-sparged water, 3 ml of N-methylpyrrolidone and 50 grams of the crude hydroformylation reaction product that was essentially free of ligands. The mixture so formed was shaken for a few minutes and then allowed to stand in a refrigerator (at about 0° C.) until all of the organic phase solidified (one to four days). The white solid (hydrate) so formed were filtered by suction filtration using a sintered glass funnel followed by washing with 350 ml methanol and then with 350 ml hexane. The solid hydrate so purified was dried under vacuum at ambient temperature.

The five crude hydroformylation reaction products were processed in the above manner. The yields of the dried hydrates and their isomeric purities (N/I) and chemical purities are shown in Table I.

TABLE I

Separation of Various Aldehyde Isomers By Forming Solid Hydrates

| | CRUDE HYDROFORMYLATION REACTION PRODUCT | | DRIED HYDRATE | | |
|---|---|---|---|---|---|
| Aldehyde | % Normal Isomer | N/I | % Normal Isomer | N/I# | % Yield |
| Heptanal | 88.4 | 7.6 | 99.9 | 4823 | 18 |
| Nonanal | 88.2 | 7.5 | 99.6 | 274 | 88 |
| Undecanal | 92.5 | 12.3 | 99.9 | 6964 | 52 |
| Tridecanal | 90.3 | 9.3 | 98.7 | 79 | 44 |
| Pentadecanal | 94.2 | 16.4 | 99.6 | 275 | 52 |

Ratio normal aldehyde to iso aldehyde as determined by Gas Chromatography

EXAMPLE II

SYNTHESIS AND PURIFICATION OF NONANAL HYDRATE 50 grams crude nonanal made by hydroformylation of 1-octene was mixed with 3 grams N-methylpyrrolidone and 100 grams water. The mixture was left in the refrigerator (about 0° C.) for five days. Large quantities of solid nonanal hydrate formed within 24 hours. The solid hydrate was filtered and washed successively with 350 ml methanol and 350 ml hexane. Samples were retained for Gas Chromatographic analysis at each stage of the washings. 44 grams of a waxy powder (purified hydrate) was isolated. The isomer content of the crude aldehyde and of the unwashed, methanol-washed and hexane-washed hydrate are given in Table II.

TABLE II

Improvement of the Linear Isomer Purity In Crude Nonanal Hydrate by Washing

| | % Normal Isomer |
|---|---|
| Crude Aldehyde | 88.2 |
| Unwashed Hydrate | 89.1 |
| Methanol-Washed Hydrate | 97.7 |
| Hexane-Washed Hydrate | 99.6 |

EXAMPLE III

SEPARATION OF ALDEHYDES CONTAINING A PHENYL GROUP

Separation of hydrocinnamic aldehyde from hydratropic aldehyde was demonstrated as follows. To a synthetic mixture containing 20 grams of hydrocinnamic aldehyde and 20 grams of hydratropic aldehyde were added 1.6 grams of N-methylpyrrolidone and 80 of grams water. The mixture was shaken vigorously. To 60 grams of the mixture was added (in an effort to catalyze hydrate formation*) 20 grams of 10 wt. % hydrochloric acid solution and the mixture was again shaken vigorously. The mixture was placed in the refrigerator for about two days. No solid product was detected on standing. However, when the mixtures were shaken while cold, a waxy solid aldehyde hydrate formed immediately. The hydrate was separated by filtration and washed with hexane. Gas chromatographic analysis of the solid hydrate (before and after hexane washing) as well as of the filtrate after separation of the solid hydrate are given in Table III.

TABLE III

Separation of Hydrocinnamic Aldehyde from Hydratropic Aldehyde by Solid Hydrate Formation

| | % Hydrocinnamic Aldehyde |
|---|---|
| Starting Mixture | 50 |
| Solid Hydrate | 58 |
| Filtrate | 34 |

TABLE III-continued

Separation of Hydrocinnamic Aldehyde from Hydratropic Aldehyde by Solid Hydrate Formation

| | % Hydrocinnamic Aldehyde |
|---|---|
| Hexane-Washed Hydrate | 63 |

*In another experiment, it was found that the hydrate formed as rapidly without added hydrochloric acid.

EXAMPLE IV

Separation Of The Normal Isomers From A Mixture Of Homologous Aldehydes

Part A - To a synthetic mixture containing 25 grams crude undecanal (made by hydroformylation of 1-decene) and 25 grams crude tridecanal (made by hydroformylation of 1-dodecene) were added 3 grams of N-methylpyrrolidone and 100 grams of water. The synthetic mixture was shaken well and left in the refrigerator (at about 0° C.) for two days. Solid hydrates of both normal aldehydes formed and were filtered from the liquid components of the synthetic mixture (e.g., the two iso aldehydes). The mixed solid hydrates so obtained were successively washed with 300 ml of methanol and 300 ml of hexane. By this process, 8.5 grams of a waxy powder (purified mixed normal aldehydes) was isolated. The isomer contents of the aldehydes and the percent olefinic contaminants in the starting mixture, crude hydrates and the washed hydrates are given in Table IV.

Part B - An experiment was run under the conditions of Part A above with the exception that the solid hydrate mixture was washed with isopropanol rather than with methanol and hexane. The isomer contents of the aldehydes and the percent olefinic contaminants in the starting mixture, crude hydrates and the washed hydrates are also given in Table IV.

TABLE IV

Separation of the Normal Aldehydes Present in Mixtures of Homologous Aldehydes via Solid Hydrate Formation

| | Undecanal (%) | N/I | Tridecanal (%) | N/I | Olefin Impurities |
|---|---|---|---|---|---|
| Crude | 38.1 | 9.8 | 35.2 | 27.7 | 21.6 |
| Mixture MeOH/hexane-washed hydrate | 39.8 | 19.9 | 46.1 | 82.4 | 11.5 |
| i-PrOH washed hydrate | 37.8 | 12.6 | 42.0 | 42 | 16.1 |

What is claimed is:

1. A process for separating an aldehyde that contains at least seven carbon atoms and that is free of alpha substituents from a solution containing the aldehyde and a non-polar organic liquid which process comprises contacting the solution with water to form a solid hydrate of the aldehyde by the reaction of the aldehyde with the water at a temperature above the melting point of the aldehyde but below the decomposition temperature of the solid hydrate and separating the solid hydrate from the solution.

2. A process as claimed in claim 1 wherein the solution is the crude reaction product of a hydroformylation process and contains an aldehyde as defined in claim 1 (first aldehyde) and an aldehyde (second aldehyde) that is an isomer of the first aldehyde and wherein the second aldehyde remains in the solution after the formation of the solid hydrate of the first aldehyde.

3. A process as claimed in claim 1 wherein the solid hydrate that is separated from the solution is then heated to regenerate the aldehyde.

4. A solid hydrate having the formula:

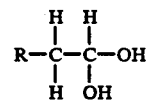

wherein R is a monovalent hydrocarbon group containing from 5 to 25 carbon atoms inclusive.

5. The solid hydrate of normal heptanal.
6. The solid hydrate of normal nonanal.
7. The solid hydrate of normal undecanal.
8. The solid hydrate of normal tridecanal.
9. The solid hydrate of normal pentadecanal.
10. The solid hydrate of normal hydrocinnamic aldehyde.

* * * * *